United States Patent [19]

Usdin

[11] Patent Number: 4,788,059
[45] Date of Patent: Nov. 29, 1988

[54] EQUINE STRANGLES VACCINE AND THE METHOD OF PREPARING AND USING THE SAME

[75] Inventor: Myron G. Usdin, Prairie Village, Kans.

[73] Assignee: Coopers Animal Health, Inc., Kansas City, Kans.

[21] Appl. No.: 754,909

[22] Filed: Jul. 15, 1985

[51] Int. Cl.$^4$ ............... A61K 39/00; A61K 37/00; C12N 15/00; C12N 1/20
[52] U.S. Cl. .............................. 424/93; 424/88; 424/92; 435/172.1; 435/253; 435/885
[58] Field of Search ............... 435/172.1, 253, 885; 424/88, 92, 93

[56] References Cited

U.S. PATENT DOCUMENTS

| 3,529,056 | 9/1970 | Engelbrecht | 424/92 |
|---|---|---|---|
| 3,793,150 | 2/1974 | Usdin | 424/92 |
| 3,852,420 | 12/1974 | Usdin | 424/92 |
| 4,328,210 | 5/1982 | Kucera | 424/92 |
| 4,335,106 | 6/1982 | Kucera | 424/92 |
| 4,626,430 | 12/1986 | Kucera | 424/92 |
| 4,681,762 | 7/1987 | Oeschger et al. | 424/92 |

OTHER PUBLICATIONS

*Manual Methods General Bacteriology* (Eds. P. Gerhardt et al) Amer. Soc. Microbiol., Wash. D.C., 1981 p. 226.
Timoney et al *Chem Abst* vol. 106(20) No. 162558x 1987, "Vaccine for the Protection of Equines Against *Streptococcus equi*".
"The Production of Filtering Forms of *Streptococcus equi* and the Study of Regenerated Cultures", Zhalobovskiy, publ. at Tr. Inst. Vet. Kazakhsk. Filiala Vses. Aka. Selskokhoz. Nauk Im. V. I. Lenina 8.201–209. 1957; Referat. Zhur., Biol., 1959, No. 91687 (English translation included).

*Primary Examiner*—Thomas G. Wiseman
*Assistant Examiner*—Robin L. Teskin
*Attorney, Agent, or Firm*—Kokjer, Kircher, Bradley, Wharton, Bowman & Johnson

[57] ABSTRACT

A vaccine for immunizing equines against strangles and a method of using the vaccine. The vaccine is made by isolating the causative organism *Streptococcus equi* (*S. equi*) from an abscess on a horse showing typical symptoms of strangles, and confirming the identity of the organism through standard biochemical techniques. The isolated *S. equi* is passed through a suitable growth medium (Todd-Hewitt broth) and two parts per million acriflavine hydrochloride is added. The acriflavine level is increased over a period of approximately eleven weeks to a concentration of about sixteen parts per million to yield an avirulent *S. equi* while retaining its antigenicity. The method of administering the vaccine consists of inoculating the horse intranasally with the attenuated *S. equi*.

4 Claims, No

EQUINE STRANGLES VACCINE AND THE METHOD OF PREPARING AND USING THE SAME

This invention relates to a vaccine for the immunizing of equines against strangles and to a method of using the vaccine.

Strangles is a highly contagious disease of horses caused by Streptococcus equi. Although the rate of mortality associated with the disease is low, it is annoying and debilitating and affects large groups of horses, especially when they are associated together in groups at race tracks, horse shows, sales lots and the like. The clinical signs of the disease include a rise in temperature, increased rate of respiration, depression, anorexia, inflammation of nasal mucosa, catarrhal discharge, swelling of lymph nodes, and development of abscesses. The causative organism, Streptococcus equi (S. equi), is very hardy and is capable of surviving for months in a stressful environment such as that found in stables and other places where horses are kept. Young horses are more susceptible to infection in view of the fact that older animals are more likely to have been in contact with the disease and developed an immunity to it. Because of the highly contagious nature of the disease, it is difficult to prevent it from spreading among horses that share common quarters.

Bacterins effective against S. equi are available and have satisfactory immunizing properties. However, commercially available bacterins which are suspensions of the killed microorganism S. equi contain extraneous protein and carbohydrate fractions, both cellular and extracellular, which are responsible for many side reactions such as purpura, swelling at the site of injection, stiffness in the joints, and transitory glandular swelling with nasal discharge. The side reactions are likely to result in inappetence, debility, loss of condition, and subclinical symptoms of the disease being treated.

My previously issued U.S. Pat. Nos. 3,793,150 and 3,852,420 relate to a vaccine effective in immunizing equines against virulent strains of S. equi including a method of preparing the vaccine and its method of use. The vaccine which is the subject of my two prior patents is based upon the identification and isolation of a highly effective antigen which causes protective antibodies against S. equi to develop when introduced into horses.

S. equi is classified as a Group C Streptococcus, the strains of which share a common group-specific polysaccharide antigen. An antigen purified from S. equi has been shown by varios researchers to be both safe and efficient in protecting against occurrence of strangles and is the basis of my previously patented vaccine. This vaccine does not, however, afford absolute protection against strangles in horses which have been immunized.

There is also evidence linking the virulence factor of Group A Streptococci, commonly found in humans, with protective antigenicity. This virulence factor and protective antigen have both been substantiated to be the M-protein.

It is also known to utilize attenuated organisms to prepare vaccines which are effective in both humans and animals. For example, U.S. Pat. No. 3,529,056 to Engelbrecht discloses a vaccine for the treatment of hog jowl abscess utilizing an attenuated strain of the causative organism Group E Streptococcus.

It has not heretofore been attempted to develop an attenuated organism effective against S. equi since it would be predicted that the commonality between the virulence factor and the protective antigen of this organism would cause the antigen to be destroyed during the process of rendering the organism avirulent.

It is, therefore, the primary object of the present invention to develop an effective vaccine against Streptococcus equi utilizing an attenuated organism.

It is also a very important objective of this invention to provide a method of immunizing equines against virulent strains of Streptococcus equi by inoculating the equine with an attenuated Streptococcus equi organism.

Further aims and objectives of the invention ancillary to those set forth above will become apparent from a reading of the detailed description and claims hereafter.

Streptococcus equi was isolated from an abscess on a horse showing typical symptoms of strangles. The identity of the organism was confirmed utilizing standard biochemical techniques well known to those skilled in the art. Virulence of the strains was confirmed utilizing mice which were injected intraperitoneally with an 18 hour culture grown in Todd-Hewitt broth.

Todd-Hewitt broth to which has been added acriflavine or acriflavine hydrochloride is a suitable medium for attenuation of the organism. The isolated S. equi is passed through the medium over a period of approximately eleven weeks during which time the acriflavine level is gradually increased according to the Table 1 schedule until a maximum concentration of sixteen parts per million is reached. The organism may be held for a period of time on a blood agar plate.

TABLE 1

| Day | Acriflavine (PPM) | Day | Acriflavine (PPM) |
| --- | --- | --- | --- |
| 1 | 2 | 68 | 6 |
| 2 | 2 | 69 | 8 |
| 4 | 2 | 70 | 10 |
| 9 | 4 | 71 | 12 |
| 10 | 4 | 76 | 12 |
| 12 | 4 | 77 | 14 |
| 14 | 4 | 78 | 16 |

Other methods of attenuation well known to those skilled in the art may be employed in conjunction with the procedure of the present invention. For example, the technique disclosed by B. P. Smith et al., Am J. Vet Res 45: 59–66 is suitable. Other acceptable procedures for attenuation of bacteria are set forth in the Englebrecht patent, previously referenced, and U.S. Pat. No. 2,980,586 to Norden et al. Both of these United States patents are incorporated by reference into the present specification, although it is to be understood that a complete understanding of the invention may be obtained by those skilled in the art from reading the present specification.

The attenuated organism may be introduced into the infected animal through various routes, although intranasally is preferred because of the effectiveness which has been shown to be obtainable through introduction at this site. A dosage of $2 \times 10^9$ C.F.U. (colony forming units) for a small pony weighing approximately 400 pounds has proven effective.

The following example illustrates the way in which the vaccine of the present invention is administered and the method of immunization utilizing the invention.

EXAMPLE

Four Shetland ponies were randomly assigned to either a control or vaccinate group. Ponies nos. 20 and 22 were inoculated intranasally with 2 ml. per nostril of reconstituted lyophilized attenuated *S. equi*. The microorganism was attenuated according to the procedure discussed above. The vial was reconstituted with 10 ml. of water. It was determined that each pony received a total dosage of $1 \times 10^9$ C.F.U. per nostril. Control ponies nos. 21 and 23 were each given 2 ml. per nostril of dilute Todd-Hewitt broth. The controls and vaccinates were isolated in separate quarters and both groups were fed the same conventional ration of prepared feed containing no antibiotics.

Twenty nine days after inoculation of the two vaccinates, all four ponies were challenged with a virulent strain of *S. equi* grown in Todd-Hewitt broth. The virulence of the microorganism was confirmed in accordance with the previously mentioned procedure. Observations were made daily for white blood cell (WBC) counts, temperature and general clinical health of the four animals.

The two vaccinates did not show any significant temperature rise when the animals were challenged with the virulent *S. equi*. The two non-vaccinates showed greater than a 100% increase in WBC count post-challenge and this elevated count lasted for several days before returning to normal. Body temperatures for the vaccinates fluctuated only within normal limits post-challenge while the non-vaccinates experienced temperature increases of 3°-4° F. above normal for several days post-challenge until the study was terminated on the thirteenth day. The two unprotected animals also manifested clinical signs of strangles while the two vaccinates remained clinically normal.

It is also within the scope of the present invention to utilize the vaccine and method herein described in combination with other vaccines such as that disclosed in my two earlier patents referenced above. Such a procedure would have the advantage of activating two immunological systems, the attenuated strain by cell mediated immunity, and the humoral system through immunization with the *S. equi* antigen administered subcutaneously or intramuscularly.

I claim:

1. A vaccine effective in protecting equines against infection by virulent strains of *Streptococcus equi* comprising an immunizing dosage of an attenuated *Streptococcus equi* organism rendered avirulent while retaining its antigenicity through prolonged culturing in the presence of acriflavine hydrochloride.

2. A vaccine as set forth in claim 1 wherein the level of attenuation of said organism is equivalent to that obtained when *Streptococcus equi* is cultured in the presence of acriflavine hydrochloride for a prolonged period of time and at gradually increasing acriflavine hydrochloride concentrations ranging from about 2 ppm to about 16 ppm.

3. A method of immunizing equines against virulent strains of *Streptococcus equi* which comprises innoculating said equines with an attenuated *Streptococcus equi* organism rendered avirulent while retaining its antigenicity through prolonged culturing in the presence of acriflavine hydrochloride.

4. A method as set forth in claim 3 wherein the level of attenuation of said organism is equivalent to that obtained when *Streptococcus equi* is cultured in the presence of acriflavine hydrochloride for a prolonged period of time and at gradually increasing acriflavine hydrochloride concentrations ranging from about 2 ppm to about 16 ppm.

* * * * *